(12) United States Patent
Porsch et al.

(10) Patent No.: US 9,095,847 B2
(45) Date of Patent: Aug. 4, 2015

(54) TAPE CASSETTE AND METHOD FOR THE MANUFACTURE THEREOF

(71) Applicant: Roche Diagnostics Operations, Inc., Fishers, IN (US)

(72) Inventors: Ulrich Porsch, Weinheim (DE); Christian Freitag, Weinolsheim (DE); Peter Seelig, Frankfurt am Main (DE); Thomas Jaeck, Heddesheim (DE); Jens Schaefer, Oberderdingen (DE)

(73) Assignee: Roche Diabetes Care, Inc., Indianapolis, IN (US)

( * ) Notice: Subject to any disclaimer, the term of this patent is extended or adjusted under 35 U.S.C. 154(b) by 90 days.

(21) Appl. No.: 13/713,153

(22) Filed: Dec. 13, 2012

(65) Prior Publication Data

US 2013/0108524 A1    May 2, 2013

Related U.S. Application Data

(63) Continuation of application No. PCT/EP2011/002792, filed on Jun. 8, 2011.

(30) Foreign Application Priority Data

Jun. 19, 2010    (EP) ..................... 10006397

(51) Int. Cl.
*B01L 3/00* (2006.01)
*A61B 5/15* (2006.01)
(Continued)

(52) U.S. Cl.
CPC ............... *B01L 3/00* (2013.01); *A61B 5/1411* (2013.01); *A61B 5/14532* (2013.01); *A61B 5/150022* (2013.01); *A61B 5/15146* (2013.01); *A61B 5/15169* (2013.01); *A61B 5/15171* (2013.01); *A61B 5/150358* (2013.01); *A61B 2562/0295* (2013.01); *G01N 2035/00019* (2013.01); *Y10T 29/49826* (2015.01)

(58) Field of Classification Search
CPC ..... G01N 33/487; G01N 33/16; G01N 31/00; G01N 35/00; G01N 33/48; G01N 33/52; G01N 21/00; G01N 21/75; G01N 33/50; G01N 21/84; G01N 2021/6439; G01N 35/00009; G01N 2035/00019; A61B 17/32; A61B 5/14532; A61B 5/150022; A61B 5/15146; A61B 5/15171; A61B 5/15169; A61B 15/0358; A61B 5/1411; A61B 2562/0295; B32P 11/00; B01L 3/00; Y10T 29/49826

See application file for complete search history.

(56) References Cited

U.S. PATENT DOCUMENTS 8,282,893 B2    10/2012    Schosnig et al.
2005/0232815 A1 *    10/2005    Ruhl et al. ............ 422/66

(Continued)

FOREIGN PATENT DOCUMENTS

DE    2803345 B1    6/1979
EP    1967139 A1    9/2008

(Continued)

*Primary Examiner* — Lore Jarrett
(74) *Attorney, Agent, or Firm* — Roche Diabetes Care, Inc.

(57) ABSTRACT

There is disclosed a tape cassette having a reeled-up carrier tape that carries at least one type of functional elements, namely test elements and/or puncturing elements, that are arranged at a distance from each other in a tape direction. The distances in the tape direction from a functional element to the next functional element of the same type change periodically in space at a period P. Moreover, there is disclosed a method for manufacture of a tape cassette of this type.

24 Claims, 2 Drawing Sheets

(51) Int. Cl.
  *A61B 5/145* (2006.01)
  *A61B 5/151* (2006.01)
  *G01N 35/00* (2006.01)

(56) References Cited

U.S. PATENT DOCUMENTS

2006/0195128 A1* 8/2006 Alden et al. .................. 606/181
2008/0286149 A1* 11/2008 Roe et al. ....................... 422/58
2010/0121369 A1   5/2010 Harttig et al.
2010/0145376 A1* 6/2010 Konya et al. .................. 606/172

FOREIGN PATENT DOCUMENTS

| EP | 1990002 A1 | 11/2008 | |
| EP | 2039294 A1 | 3/2009 | |
| WO | 2004/060174 A2 | 7/2004 | |
| WO | WO2008138473 * | 11/2008 | ............. G01N 35/00 |
| WO | 2009/086907 A1 | 7/2009 | |

* cited by examiner

TAPE CASSETTE AND METHOD FOR THE MANUFACTURE THEREOF

CROSS-REFERENCE TO RELATED APPLICATIONS

The present application is a continuation of International Patent Application No. PCT/EP2011/002792 filed on Jun. 8, 2011, which claims priority to European Application No. 10006397.3 filed on Jun. 19, 2010. Each of the referenced applications is incorporated herein by reference.

FIELD OF THE INVENTION

The invention is related to a tape cassette having a reeled-up carrier tape that carries test elements with detection regions for analysis of a sample of a human or animal body fluid.

BACKGROUND

Tape cassettes can be a part of systems for measuring analyte concentrations in body fluid. Systems of this type are needed, for example, by diabetics who have to measure the glucose content of a sample of body fluid, typically blood and/or interstitial fluid, several times daily. Lactate or hemoglobin concentrations, for example, are other analyte concentrations that can be measured with systems of this type.

A carrier tape of such tape cassettes can carry test elements, for example test fields with detection reagents, and/or puncturing elements as functional elements. In the case of tape cassettes designed for devices that are strictly measuring devices, the carrier tape carries only one type of functional elements, namely test elements. Likewise, only a single type of functional elements, namely puncturing elements, is arranged on the carrier tape of a tape cassette for a system that is strictly a puncturing system. In the case of integrated measuring and puncturing devices, two types of functional elements can be arranged on a carrier tape, namely test elements as first type and puncturing element as second type. Moreover, in the case of tape cassettes for integrated measuring and puncturing devices it is also feasible to arrange only a single type of functional elements on the carrier tape, namely puncturing elements with integrated test elements.

One advantage of tape cassettes is that a very large number of functional elements, for example 50 or even more test elements, can be arranged on a carrier tape that is reeled up in the tape cassette. However, further improvements in this technological area are needed.

SUMMARY

There is disclosed herein a way that allows the number of test elements contained in a tape cassette to be increased without enlarging the tape cassette.

According to one aspect, a tape cassette is disclosed having a reeled-up carrier tape that carries test elements with detection regions for analysis of a sample of a human or animal body fluid that are arranged at a distance from each other in a tape direction. The distances in the tape direction from a test element to the next test element change periodically in space at a period P. In another aspect, a method is disclosed for the manufacture of a tape cassette. Test elements and/or uniformly oriented puncturing elements are arranged as functional elements on a carrier tape. The carrier tape is subsequently reeled-up and introduced into a cassette housing. The functional elements are arranged on the carrier tape at periodically changing distances.

In a tape cassette according to one embodiment, the test elements are not arranged at constant distances from each other. Rather, the distances in tape direction from a test element to the next test element change periodically such that the distances between a test element and the next test element are repeated after a given number of test elements, i.e. after a given number of identical functional elements.

Reeling up a conventional carrier tape on which functional elements are arranged at constant distances, it can happen that test elements are situated directly over each other in the reeled-up carrier tape. In this case, the reeled-up carrier tape can form an imperfectly round reel that has a larger radius in places, in which many test elements are situated over each other, as compared to other places. The design space available in a tape cassette is utilized poorly by an imperfectly round reel of this type. It is disclosed herein that the distances in the tape direction from one test element to the next test element change periodically in space, allowing a more even distribution of functional elements in circumferential direction of a carrier tape reel to be attained. The cross-section of the reeled-up carrier tape is therefore closer to the ideal circular shape such that the space available in the cassette can be utilized better.

Accordingly, there is disclosed, for example, a tape cassette having a reeled-up carrier tape that carries test elements, whereby the distances in the tape direction from one test element to the next test element change periodically in space at a period of P. The carrier tape can also, in addition, carry puncturing elements. It is also feasible to provide the test elements as integrated puncturing and test elements.

Moreover, there is disclosed a tape cassette having a reeled-up carrier tape that carries uniformly oriented puncturing elements, whereby the distances in the tape direction from one puncturing element to the next puncturing element change periodically in space at a period of P. Uniformly oriented puncturing elements all point in the same direction with respect to the tape. In other words, uniformly oriented puncturing elements all point to the same edge of a tape, e.g. all puncturing elements point to the same lateral edge or all puncturing elements point in the tape direction, for example all to the forward edge or end of the tape.

Another embodiment provides the distances between functional elements of the same type within period P to change by more than the length of a functional element as measured in the tape direction. This means that the largest distance from a functional element to the next functional element of the same type differs from the smallest distance between two functional elements of the same type by more than the length of one functional element as measured in the tape direction.

Another embodiment provides the distances, in the tape direction and within period P, from a functional element to the next functional element of the same type to vary by at least 5%, preferably by at least 10%. Accordingly, within period P, the difference between the largest distance and the smallest distance from a functional element to the next functional element of the same type is at least 5% of the smallest distance, at least 10%, and/or at least 15%.

What can be attained by means of the measures described above is that the distances between identical puncturing elements, i.e. puncturing elements of the same type, vary strongly enough to effect a more even distribution of functional elements in circumferential direction in a reeled-up carrier tape.

Another embodiment provides the difference, within period P, between the largest distance and the smallest distance from a functional element to the next functional element of the same type to be no more than 50%, no more than 40%, and/or no more than 30% of the smallest distance. Unnecessarily large variations of the distance between consecutive functional elements of the same type do not lead to improved reeling properties of the tape, but mainly result in poorer utilization of the carrier tape such that an unnecessarily small number of functional elements per unit length are arranged on the carrier tape.

Another embodiment provides a period P to comprise at least three functional elements of the same type, e.g. at least three test elements. This means that the distances between consecutive functional elements of the same type are repeated after three or more functional elements of the same type. Although improved reeling properties of the carrier tape can also be attained by means of a shorter period that comprises just two functional elements of the same type, i.e. just two different distances, the variation options with a period being this short are low such that there are limits with regard to the possible improvement of the reeling properties of a carrier tape.

Another embodiment provides a period to comprise at most 10, at most 8, at most 6, and/or at most 5 functional elements of the same type. Namely, if a faulty functional element is placed on the carrier tape or a functional element is arranged in an incorrect position during the production process, it is feasible to cut an entire period, which includes the faulty test element, from the carrier tape and connect the two tape ends thus generated to each other, for example by gluing or welding them together. In this case, the loss of functional elements is the larger the more functional elements are included in a period. Limiting the number of identical functional elements in a period to at most 10, at most 6, and/or at most 5 functional elements, allows unnecessary production losses to be prevented and good reeling properties of the carrier tape to still be attained. It is particularly advantageous to have, for example, 3 to 5 functional elements of the same type per period.

The periodical arrangement of the functional elements on the carrier tape refers to the nominal positions of the functional elements that are the aim in the production process. Obviously, production tolerances cannot be prevented altogether in the scope of a production process such that the actual positions of the functional elements vary from the nominal positions by the production tolerances. These deviations from the nominal positions are distributed randomly. For this reason, the distances in the tape direction from a functional element to the next functional element of the same type in a carrier tape disclosed herein change periodically in space at a period P within production tolerances.

Typically, the periodical change, i.e. the difference between the largest distance between identical functional elements and the smallest distance between identical functional elements in a period, equals at least 5 times, in particular at least 10 times, in particular 20 times the production-related tolerance deviations of the actual positions from the nominal positions.

In addition, the carrier tape may comprise position markers that are assigned to one functional element each. The position markers can, for example, be holes or can be printed onto the carrier tape. The position markers can be used in the production process to define the positions in which functional elements are applied to the carrier tape. Moreover, the position markers be used by a device, in which a tape cassette disclosed herein is inserted, to stop tape transport at a defined place in order to position a functional element precisely for a subsequent use. The distances in tape direction from position marker of a test element and the next position marker of a test element may then change periodically in space at a period of P.

BRIEF DESCRIPTION OF THE FIGURES

Further details of the invention shall be illustrated in the following based on exemplary embodiments and by referring to the appended drawings. In this context, identical and equivalent components are identified by the same reference numbers.

DETAILED DESCRIPTION

Figure 1:
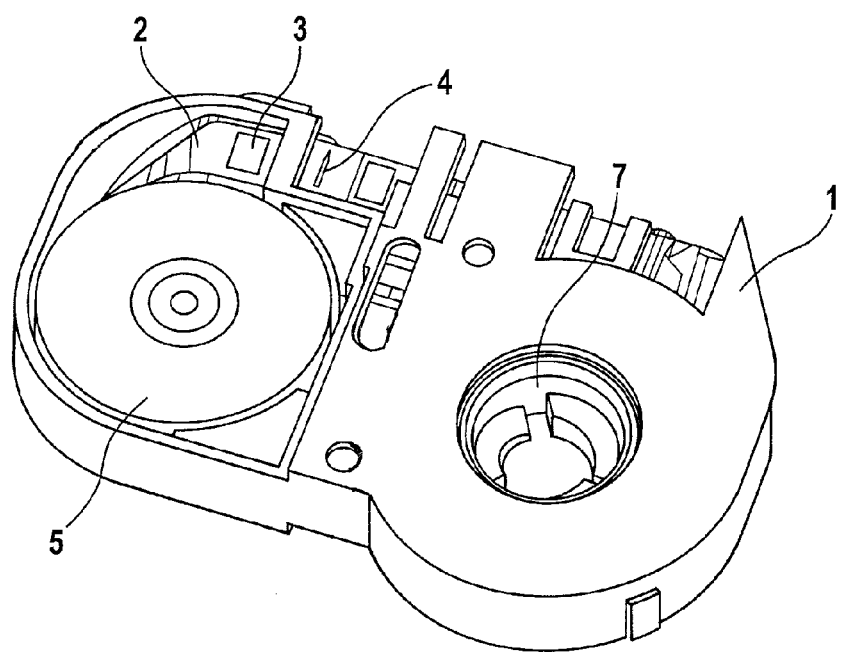
FIG. 1 shows a schematic view of an exemplary embodiment of a tape cassette.

For the purposes of promoting an understanding of the principles of the invention, reference will now be made to the embodiments illustrated in the drawings and specific language will be used to describe the same. It will nevertheless be understood that no limitation of the scope of the invention is thereby intended, any alterations and further modifications in the illustrated embodiments, and any further applications of the principles of the invention as illustrated therein as would normally occur to one skilled in the art to which the invention relates are contemplated herein.

FIG. 1 shows an exemplary embodiment of a tape cassette having a cassette housing 1 that contains a carrier tape 2 that carries functional elements, namely test elements 3 with detection reagents for analysis of a sample of a human or animal body fluid, as well as puncturing elements 4. The section of the carrier tape 2 carrying unused functional elements is reeled onto a reel 5. Sections of the carrier tape 2 having used functional elements are reeled onto a second reel 7. Carrier tape 2 is a film with a thickness of, for example, 0.1 mm to 0.2 mm. Test fields 3 can be of comparable thickness such that the total thickness of the configured carrier tape 2 between regions carrying functional elements 3, 4 and free regions may vary by a factor of 2 or more.

Figure 2:
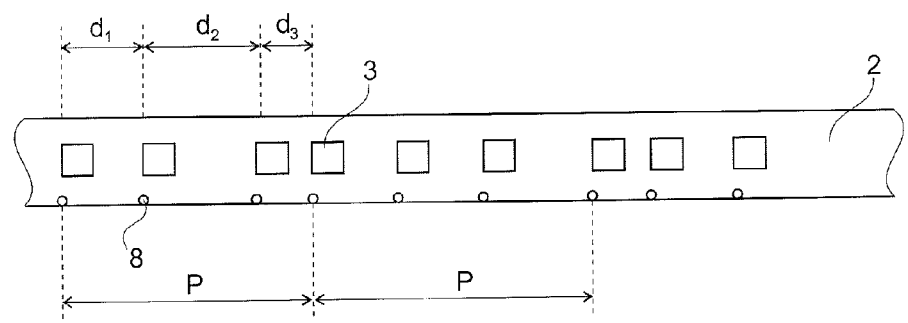
FIG. 2 shows a schematic view of functional elements being arranged on a carrier tape.

Carrier tape 2 can be configured with only a single type of functional elements, for example in that it carries only test elements 3 or only puncturing elements 4. FIG. 2 shows an exemplary embodiment, in which carrier tape 2 carries only test elements 3 as functional elements. Moreover, it is also feasible to configure carrier tape 2 with two different types of functional elements, namely with both test elements 3 and puncturing elements 4. One exemplary embodiment of this case is shown schematically in FIG. 3. As can be seen, all puncturing elements 4 are oriented in the same direction. With other words, all puncturing elements 4 point to the same edge of the carrier tape.

Figure 3:
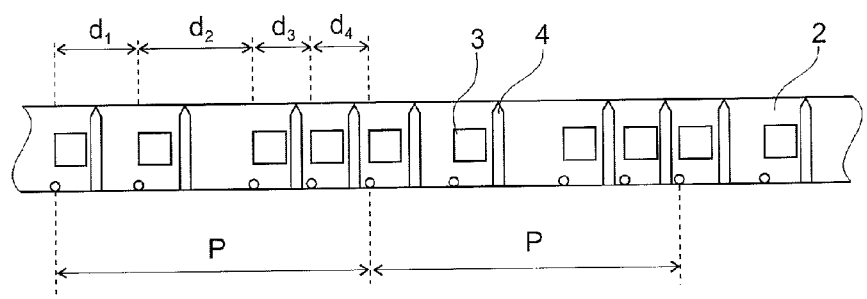
FIG. 3 shows another exemplary embodiment of functional elements being arranged on a carrier tape.

FIG. 2 clearly shows that the distances in tape direction from a functional element 3 to the next functional element 3 of the same type change periodically in space at a period P. In the exemplary embodiment shown in FIG. 2, a period P includes three functional elements of the same type, namely three test elements 3. FIG. 3 shows another exemplary embodiment, in which a period P includes four functional elements of the same type, namely four test fields 3 and four puncturing elements 4.

The length ratios are not shown to scale in FIGS. 2 and 3. The distances in tape direction from a functional element to the next functional element of the same type can, for example, be d1=129 mm, d2=110 mm, and d3=108 mm, in the exemplary embodiment shown in FIG. 2. The total length of a period P then is the sum of the individual distances d1, d2, and d3, and equals, for example, 347 mm. The length of the functional element measured in tape direction, i.e. the length of test element 3, is 10 mm in the exemplary embodiment shown in FIG. 2. Accordingly, the distances change within period P by more than the length of a functional element as measured in tape direction.

The distances between consecutive functional elements of the same type in the exemplary embodiment shown in FIG. 3 are, for example, d1=114 mm, d2=127 mm, d3=100 mm, and d4=98 mm. The puncturing elements 4 in this exemplary embodiment are arranged at a constant distance with respect to the subsequent test element 3 in the direction of tape transport such that the same distances d1, d2, d3, and d4 apply to the distances between consecutive puncturing elements.

The specified distances between neighboring functional elements include the length of the individual functional elements. Accordingly, the distance must be measured in each case between the centers of a functional element or between corresponding edges of neighboring functional elements, e.g. between a trailing edge each with respect to the direction of tape transport or between a leading edge each in the direction of tape transport.

In both exemplary embodiments, the distances within period P change by more than 10%. The difference between the largest distance and the smallest distance is d1−d3=129 mm−108 mm=21 mm in the exemplary embodiment shown in FIG. 2. This is a difference of more than 19% with respect to the smallest distance. The difference between the largest distance and the smallest distance is d2−d4=127 mm−98 mm=29 mm in the exemplary embodiment shown in FIG. 3. This is a difference of more than 29% with respect to the smallest distance from a functional element to the next functional element of said period. In one embodiment, the difference between the largest distance and the smallest distance from a functional element to the next functional element of the same type within period P is between 10% and 35% with respect to the smallest distance.

The average distance in tape direction from a functional element to the next functional element of the same type, calculated as the arithmetic mean of all distances, within period P is (d1+d2+d3)/3=115 mm in the exemplary embodiment of FIG. 2. The largest distance, namely d2, deviates from this value by 14 mm, whereas the smallest distance, namely d3, deviates by only 7 mm. The deviations of the largest and the smallest distance from the average distance therefore differ by a factor of 2.

Accordingly, the average distance from a functional element to the next functional element of the same type is (d1+d2+d3+d4)14=110 mm in the exemplary embodiment that is shown schematically in FIG. 3. The largest distance, namely d2, deviates by 27 mm from this value. The smallest distance, namely d4, deviates by 11 mm. The deviations of the largest and the smallest distance from the average distance therefore differ by a factor of more than 2.

In an exemplary embodiment that is not shown, the period P includes five functional elements of the same type, i.e. for example five test fields 3. Advantageous distances between consecutive test fields are, for example, d1=102 mm, d2=100 mm, d3=105 mm, d4=104 mm, and d5=121 mm.

For fabrication thereof, a carrier tape 2 is first provided with position markers 8 which define nominal positions of the individual functional elements. Subsequently, the functional elements are applied to the carrier tape 2 at the position markers 8. Possible deviations of the actual position of the functional elements from the nominal position defined by the position markers are negligibly small as compared to the changes of distances within one period P. In the numerical examples provided for FIGS. 2 and 3, the positional uncertainty of the individual position elements is less than 1 mm. The periodical changes of the distances therefore are larger than ten-times the positional uncertainties.

Subsequently, the carrier tape configured with functional elements is reeled onto the reel 5 of a cassette, which may have a radius, for example, of 4 mm.

The optimal distances between functional elements of the same type depend, amongst other factors, on the thickness of the carrier tape, the height of the functional element on the carrier tape, and the radius of the reel onto which the carrier tape is reeled. Advantageous distances leading to a more even distribution of the functional elements in circumferential directions in the process of reeling can be determined by trial or by numerical simulation. In this context, the above-mentioned ratios of the distances of identical functional elements within a period P specified for exemplary purposes can be used as reference points for the determination of favorable distances in any such case.

While the invention has been illustrated and described in detail in the drawings and foregoing description, the same is to be considered as illustrative and not restrictive in character, it being understood that only certain exemplary embodiments have been shown and described and that all changes and modifications that come within the spirit of the inventions are desired to be protected. In reading the claims, it is intended that when words such as "a," "an," "at least one," or "at least one portion" are used there is no intention to limit the claim to only one item unless specifically stated to the contrary in the claim. When the language "at least a portion" and/or "a portion" is used the item can include a portion and/or the entire item unless specifically stated to the contrary.

What is claimed is:
1. A tape cassette comprising:
a reeled-up carrier tape that carries non-uniformly distributed test elements with detection regions for analysis of a sample of a human or animal body fluid that are arranged at a distance from each other in a tape direction, wherein the distances in the tape direction from a test element to the next test element change periodically in space at a uniform or constant period P, wherein each period P comprises a plurality of test elements, and wherein each period P includes an identical number of test elements.

2. The tape cassette according to claim 1, wherein the distances within period P change by more than a length of one test element as measured in the tape direction.

3. The tape cassette according to claim 1, wherein the distances within period P vary at least 5%.

4. The tape cassette according to claim 1, wherein the distances within period P vary at least 10%.

5. The tape cassette according to claim 1, wherein within period P there is a difference between a largest distance and a smallest distance in the tape direction from a test element to the next test element of at least 5% of the smallest distance.

6. The tape cassette according to claim 5, wherein the difference is at least 10%.

7. The tape cassette according to claim 1, wherein within period P there is a difference between a largest distance and a smallest distance in the tape direction from a test element to the next test element of no more than 50% of the smallest distance.

8. The tape cassette according to claim 7, wherein the difference is no more than 40%.

9. The tape cassette according to claim 7, wherein the difference is no more than 35%.

10. The tape cassette according to claim 7, wherein a deviation of the largest and the smallest distance, within period P and in the tape direction, from a test element to the next test element, from an average distance differs by at least half, said distance being calculated as the arithmetic mean of all distances, within period P and in the tape direction, from the test element to the next test element.

11. The tape cassette according to claim 10, wherein the deviation from the average distance differs by at least a factor of two.

12. The tape cassette according to claim 1, wherein the period P comprises at least 3 test elements.

13. The tape cassette according to claim 1, wherein the period P comprises at most 8 test elements.

14. The tape cassette according to claim 1, wherein the period P comprises at most 6 test elements.

15. The tape cassette according to claim 1, wherein the period P comprises at most 5 test elements.

16. The tape cassette according to claim 1, wherein the carrier tape comprises at least 10 periods P.

17. The tape cassette according to claim 1, wherein the carrier tape comprises at most 30 periods P.

18. The tape cassette according to claim 1, wherein the carrier tape carries puncturing elements arranged at a constant distance with respect to an associated test element.

19. The tape cassette according to claim 18, wherein all puncturing elements are oriented in the same direction.

20. The tape cassette according to claim 1, wherein the carrier tape comprises non-uniformly distributed position markers that define nominal positions for individual test elements or puncturing elements, and wherein at each of which one test element or puncturing element is arranged.

21. The tape cassette according to claim 20, wherein the distance in the tape direction between position markers changes periodically in space.

22. A method of manufacturing a tape cassette, comprising:

arranging test elements as functional elements on a carrier tape at non-uniformly and at periodically changing distances from one another in a uniform or constant period P, wherein each period P comprises a plurality of functional elements, and wherein each period P includes an identical number of functional elements; and reeling up the carrier tape for introduction into a cassette housing.

23. The method according to claim 22, wherein position markers are provided non-uniformly and at pre-determined locations on the carrier tape first, and then the functional elements are arranged at positions on the carrier tape that are defined by the position markers.

24. The method according to claim 22, further comprising arranging uniformly oriented puncturing elements on the carrier tape at the periodically changing distances.

* * * * *